(12) United States Patent
Borkan

(10) Patent No.: US 6,832,115 B2
(45) Date of Patent: Dec. 14, 2004

(54) CATHETER LEADS FOR THE INTRATHECAL SPACE AND METHOD OF USE

(76) Inventor: William N. Borkan, 3142 NE. 166th St., North Miami Beach, FL (US) 33160

( * ) Notice: Subject to any disclaimer, the term of this patent is extended or adjusted under 35 U.S.C. 154(b) by 432 days.

(21) Appl. No.: 09/837,471

(22) Filed: Apr. 19, 2001

(65) Prior Publication Data

US 2002/0156512 A1 Oct. 24, 2002

Related U.S. Application Data

(60) Provisional application No. 60/225,823, filed on Aug. 17, 2000.

(51) Int. Cl.[7] .............................................. A61N 1/00
(52) U.S. Cl. ..................................... 607/117; 604/20
(58) Field of Search ................................ 607/117, 116; 604/20, 21, 27, 48, 500, 507, 508, 113, 512, 523, 528

(56) References Cited

U.S. PATENT DOCUMENTS

| | | |
|---|---|---|
| 3,449,768 A | 6/1969 | Doyle |
| 3,727,616 A | 4/1973 | Lenzkes |
| 4,379,462 A | 4/1983 | Borkan et al. |
| 4,414,986 A | 11/1983 | Dickhudt et al. |
| 4,459,989 A | 7/1984 | Borkan |
| 4,612,934 A | 9/1986 | Borkan |
| 4,793,353 A | 12/1988 | Borkan |
| 5,374,285 A | 12/1994 | Vaiani et al. |
| 5,423,877 A | 6/1995 | Mackey |
| 5,782,760 A | 7/1998 | Schaer |
| 5,891,094 A | 4/1999 | Masterson et al. |
| 5,938,690 A | 8/1999 | Law et al. |
| 6,099,514 A | 8/2000 | Sharkey et al. |
| 6,237,605 B1 | 5/2001 | Vaska et al. |
| 6,302,898 B1 | 10/2001 | Edwards et al. |

FOREIGN PATENT DOCUMENTS

WO          WO 00/40294           7/2000

OTHER PUBLICATIONS

"MR temperature mapping in local drug delivery and thermotherapy", MEDICA MUNDI 44/3 Nov. 2000.*
"Light–activated drug shrinks plaque buildup in arteries", Stanford Online Report, Issue of Apr. 7, 1999.*
"Light–activated drug zaps clogs in arteries" by Tim Bonfield, The Cincinnati Enquirer, Mar. 5, 2000.*

* cited by examiner

Primary Examiner—Thor Campbell
(74) Attorney, Agent, or Firm—Barnes & Thornburg LLP

(57) ABSTRACT

Various stimulation catheters are disclosed to lie along and stimulate tissue in the intrathecal space. The electrodes on the leads are various sizes to conserve the battery as well as allowing a more defined area of stimulation. It may also include multiple channels or passages for delivery of drugs, thermal or photonic energy. The sheath includes a fixing element configured to fix the electrode in place along the tissue.

8 Claims, 6 Drawing Sheets

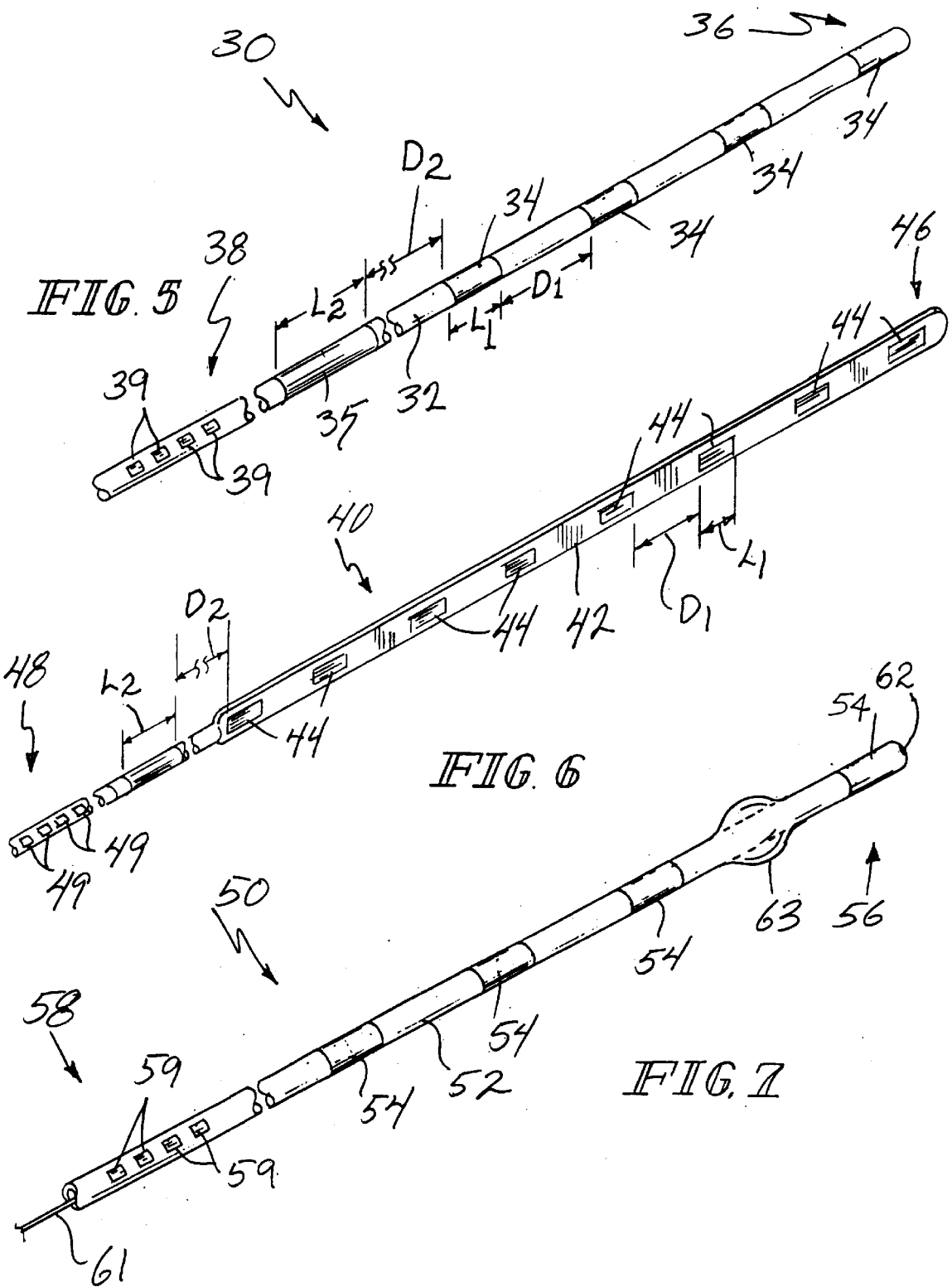

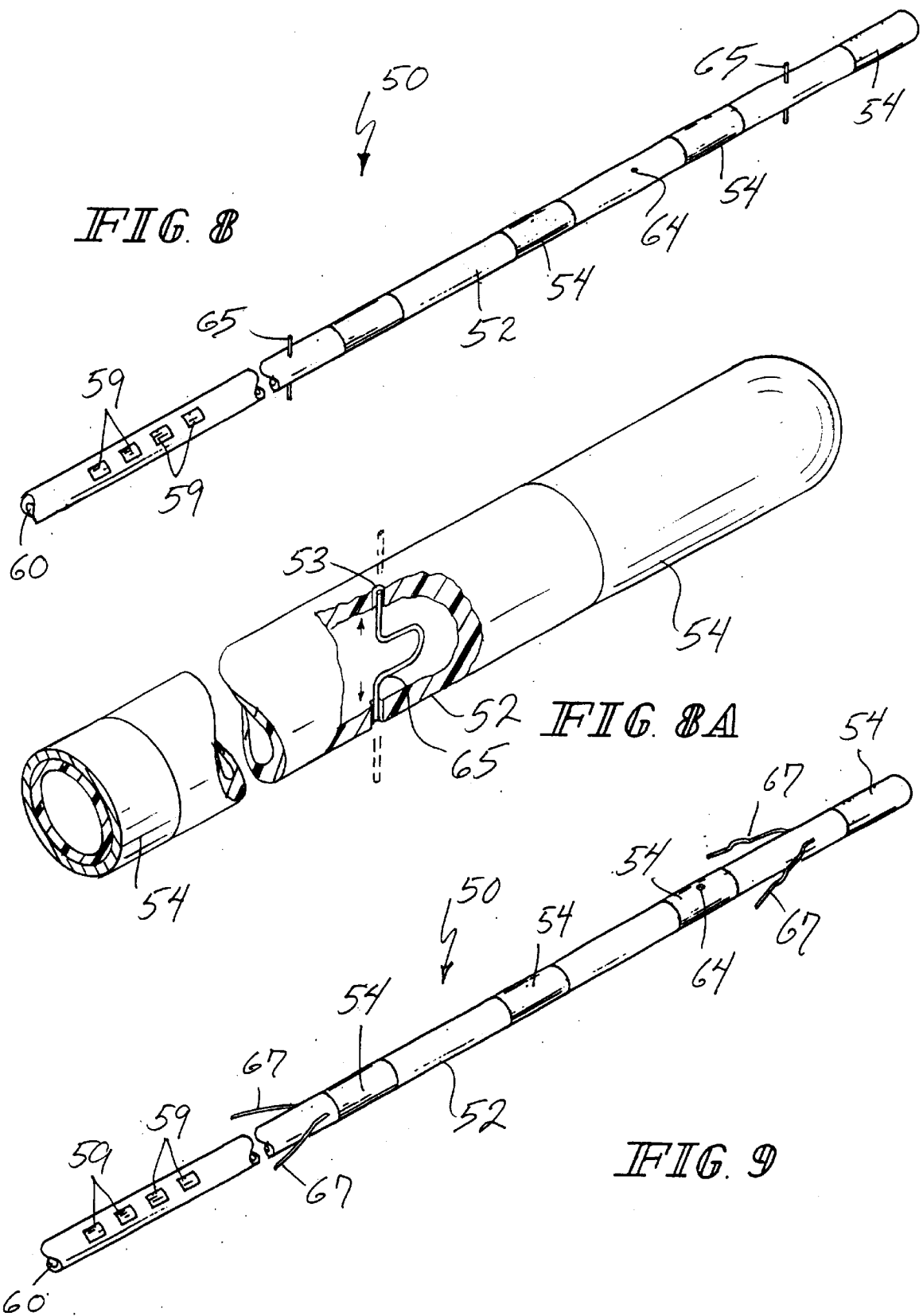

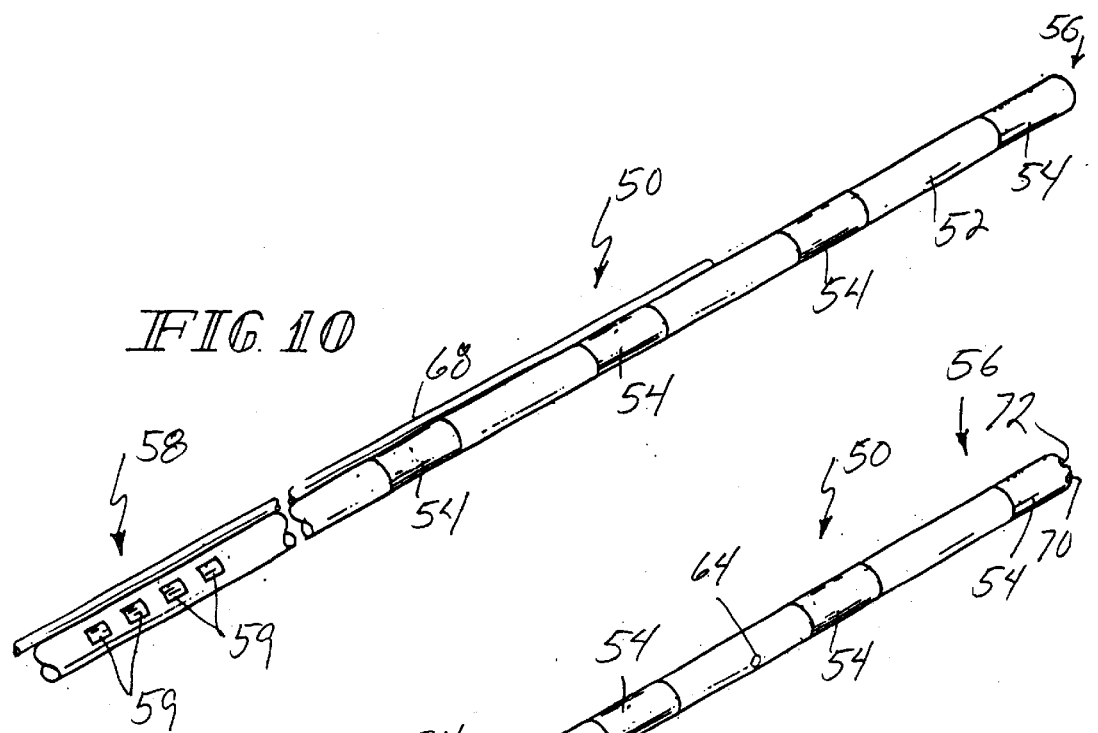
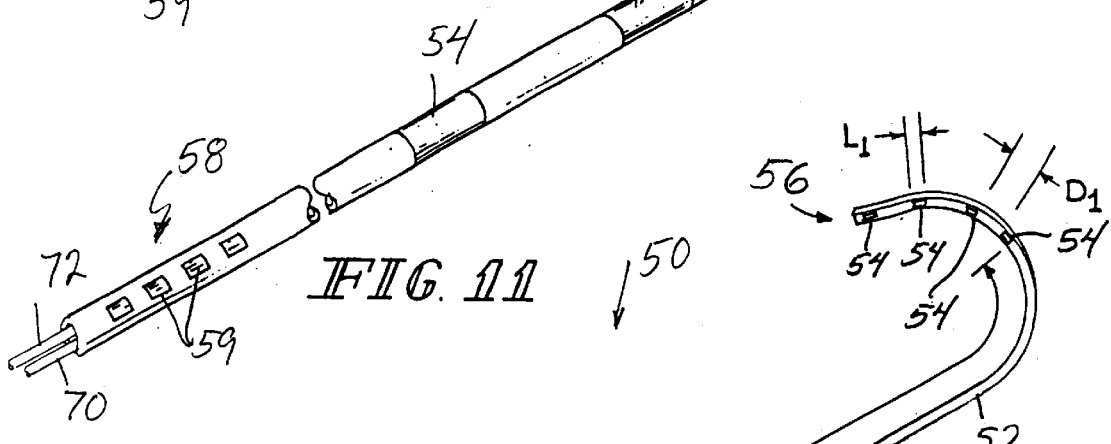
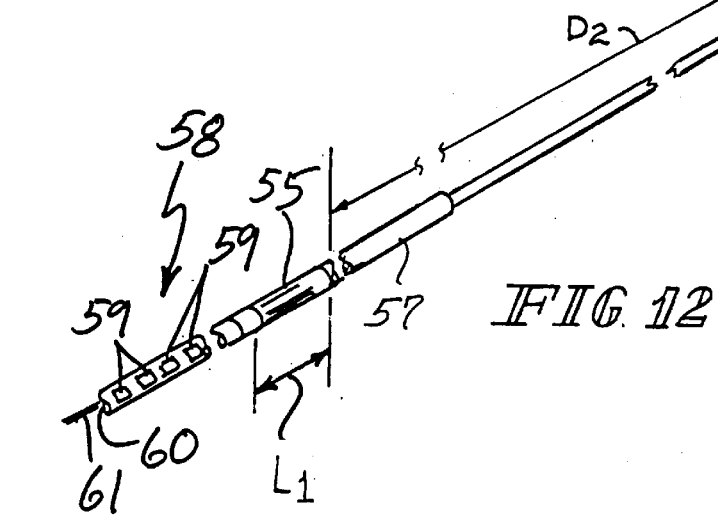

CATHETER LEADS FOR THE INTRATHECAL SPACE AND METHOD OF USE

CROSS-REFERENCE

This application claims priority of Provisional Application Ser. No. 60/225,823 filed Aug. 17, 2000.

BACKGROUND AND SUMMARY OF THE INVENTION

The present invention relates to an implanted tissue stimulator system and catheters and more specifically for use in the intrathecal space.

The concept of using electronic stimulation systems for the purpose of controlling nerves or muscles is well known. These systems typically utilize an implantable or an external pulse generator. The external systems consist of a transmitter and antenna which transmits energy and/or stimulation signals transcutaneously through a patient's skin to an implanted receiver. The receiver provides signal processing of the received pulses and transmits the energy derived therefrom to activate electrodes implanted adjacent to specific types of tissue to be stimulated. A system like the one described above has been disclosed previously in U.S. Pat. No. 3,727,616. It is also known in prior art where more than one pair of electrodes are activated such as U.S. Pat. No. 3,449,768.

Problems arise in these prior art systems where electrode placement fails to provide the desired physical response. It may also occur later if a change in patient condition or electrode position occurs. This failure may also be caused by improper polarity of the stimulated electrodes relative to one another. Furthermore, it is often required that the electrodes be implanted surgically adjacent to one or more nerve fibers. This type of procedure involves inherent risks due to the fact that it is often performed in close proximity to the brain or spinal cord or other sensitive nerves or tissues. It is therefore desirable to perform the electrode implantation only once to minimize the surgical risks to the patient as well as the financial burdens. Moreover, even when a plurality of electrodes have been utilized, such that repeated surgical procedures are not required, the prior art systems did not provide for dynamic programming and reprogramming of different electrodes after surgery until U.S. Pat. No. 4,459,989 to Borkan.

The Borkan patent '989 disclosed an external stimulator system which allowed noninvasive programming of the stimulated electrodes. Each electrode was capable of assuming a positive, negative or open circuit status with respect to the other electrodes. This effectively allowed the electrodes to be "repositioned" non-invasively. That same programming ability (plus/minus/off) was later applied to totally implantable systems as well. The system had mono/biphasic control also. Further improvements are described in U.S. Pat. No. 4,612,934 also to Borkan.

The application of spinal cord stimulation has shown itself to be effective in the treatment of pain and is under study for various other medical conditions. Initially, the leads were implanted by laminectomy and applied to the dura in the epidural space. The next generation of electrodes were positioned by percutaneous implantation. These were either placed into the intrathecal space or the epidural space. Due to the construction and nature of the electrodes used at that time (approximately 30 years ago), numerous complications occurred with the use of intrathecal catheter electrodes. These included CSF leakage. In addition, intrathecal electrodes were prone to significant movement and migration (as were the early epidural leads).

Therefore, development efforts were focused on percutaneous implantations in the epidural space. An example of a multielectrode catheter assembly for spinal cord stimulation is shown in U.S. Pat. No. 4,379,462 to Borkan.

Advances in catheter technology have allowed the widespread application of intrathecal catheters that deliver drugs for various medical applications. In addition, various fixation means for catheters have been developed and successfully utilized to eliminate the problem of electrode movement and migration. Therefore, it is now possible to develop a catheter electrode for placement into the intrathecal space without the problems and complications experienced previously.

The recent use of totally implantable stimulator systems with an implanted power source have resulted in increased emphasis on the amount of power required to deliver an effective stimulation regimen. In addition, use of multielectrode systems has put an even greater strain on the limited resources of an implanted power cell.

The intrathecal space provides a more direct means of delivering either drugs or electrical stimulation to the spinal cord. By definition, implantation of devices in the epidural space place stimulation or drugs outside the dura, significantly further away from the spinal cord. Intrathecal placement therefore allows significantly reduced levels of stimulation and drugs to create the same effect as a catheter placed epidurally.

Various stimulation catheters are disclosed to lie along and stimulate tissue in the intrathecal space. The electrodes on the leads are various sizes to conserve the battery as well as allowing a more defined area of stimulation. It may also include multiple channels or passages for delivery of drugs, thermal or photonic energy. The sheath includes a fixing element configured to fix the electrode in place along the tissue.

One embodiment of the intrathecal stimulation lead includes a sheath having at least one electrode along the exterior of a distal end of the sheath to lie in-line along the tissue. The fixing element may include at least one of the following: inflatable balloons, nitinol, tines and the sheath shape.

The sheath also include a passage extending from an inlet at the proximal end of the sheath to one or more outlets at the distal end of the sheath. The outlets may be located at one or more locations including, but not limited to, the area between the electrodes and on the electrodes. This passage may be used for dispensing of drugs. It may also be an optical channel or for a stilet to be used during positioning of the lead. This may be used without fixing elements.

Alternatively, one or more optical channels can be provided extending from a port at the proximal end of the sheath to a port at the distal end of the sheath. The port for the optical channel at the distal end may be located at one or more of the tip of the distal end, the area between the electrodes and on the electrodes. The optical channel can provide photonic energy to the tissue as well as functioning as a lens for a remote camera. The passage which extends from the inlet of the proximal end of the sheath to one or more outlets at the distal end of the sheath may be used with at least one electrode along the exterior of the sheath to lie along the tissue to be stimulated. The same passage (or another) may also allow the use of a stilet during positioning of the lead.

In one embodiment, the electrodes extend no greater than 270° about the exterior of the sheath. The leads can extend anywhere in the range of 30°–270°. This reduces the surface area of the electrodes and therefore the power required by the battery. It also allows the electrodes to have a more defined or localized stimulation. Wherein the electrodes extend less than 360° about the exterior of the sheath, the length of the each electrode along the sheath should be typically at least three millimeters. If the electrodes extends 360° about the sheath, the length of the electrodes along the sheath typically would be three millimeters or less. The currently preferred length is two to four millimeters.

In another embodiment, an additional electrode spaced along the length of the sheath from at least three in-line electrodes at the distal end of the sheath. By positioning the additional lead on the sheath it is closer to the distal electrodes and thereby reduces the current path compared to using the stimulator casing as the additional lead in a monopolar mode. The additional electrode has a surface area on the sheath greater than the surface area on the sheath of each the at least three electrodes. The additional electrode is typically at least twice the surface of the at least three electrodes and may be spaced, for example, at least 10 millimeters from the other electrodes. The increase in surface area can be by varying the length along the sheath or diminishing the circumference around the sheath of the electrodes. The lead may be activated in either a bipolar mode using two of the at least three electrodes and in a monopolar mode using the additional electrode as a common anode and at least one of the other electrodes as a cathode.

A method of neurostimulation according to the invention includes inserting a catheter electrode assembly into the intrathecal space and positioning it adjacent to the spinal cord. The catheter electrode includes a sheath having a distal and proximal end and at least three in-line electrodes along the exterior as well as a fixing element to fix the electrode in place along the spinal cord. The electrodes are fixed at a desired location along the spinal cord using the fixing element. The stimulation pulses are provided to one or more of the electrodes. Where the catheter includes a passage with one or more ports at the distal end of the catheter, the method further includes administering a drug through the passage.

The invention also anticipates an embodiment wherein the electrodes extend no greater than 60° about the exterior of the sheath, the electrodes are positioned along the nerve root where it enters the spinal cord (dorsal root entry zone). Alternatively, where the electrodes extend no greater than 90° about the exterior of the sheath, the electrodes may be positioned along the midline of the spinal cord to stimulate only the longitudinal and not the bending nerve fibers.

The catheter of the present invention can also be used for a drug treatment method. This method includes positioning a stimulation catheter adjacent to the tissue to be treated by the drug and administering a drug to the patient via the catheter. The tissue is then stimulated using the catheter. The catheter may include one or more contacts at the distal end if the catheter stimulation is by electric energy. As an alternative or in combination, an optical channel with one or more ports at the distal end of the catheter would provide stimulation by photonic energy. Alternatively, drugs may be administered systematically or concurrently with intrathecally administered agents.

The drug administered may be selected to be responsive to stimulation. Wherein the drug is responsive to light energy with a specific wavelength, the stimulation of the tissue is with the light energy of that specific wavelength using the catheter. Wherein the drug is responsive to heat or cold, the tissue is stimulated with heat or cold using the catheter. The heat may be produced by electrical energy or photonic energy. The cold may be produced by a Peltier effect device or other means for example gas or liquids. An additional optical channel with a port at the distal end of the catheter may be provided and is used to position the optical channel.

Finally, intrathecal stimulation by light energy may be administered via the catheter—with or without drugs or electrical stimulation—to activate certain tissues. These tissues may, in some cases, be treated in some manner to increase their sensitivity to this method of activation and maybe used in combination with electrical stimulation.

Other objects, advantages and novel features of the present invention will become apparent from the following detailed description of the invention when considered in conjunction with the accompanying drawings.

BRIEF DESCRIPTION OF THE DRAWINGS

FIG. 5 is a perspective view of a catheter lead with an additional common anode electrode according to the principles of the present invention.

FIG. 6 is a perspective view of another catheter lead with an additional common anode electrode.

FIG. 7 is a perspective view of a catheter lead including a passage having an outlet at the tip of the electrode and a balloon fixation device. Provision for an optional stilet is also shown.

FIG. 8 is a perspective view of a catheter lead with an outlet between the electrodes and a nitinol fixation device deployed according to the principles of the present invention.

FIG. 8A shows the nitinol fixation device in position prior to deployment.

FIG. 9 is a perspective view of a catheter lead with a passage having an outlet on the electrode and a tine fixation device according to the principles of the present invention.

FIG. 10 is a perspective view of a catheter lead wherein the passage is external the sheath according to the principles of the present invention.

FIG. 11 is a perspective view of a catheter electrode with a passage as well as two optical channels according to the principles of the present invention.

FIG. 12 is a nerve cuff lead employing the common anode principles of the present invention.

DETAILED DESCRIPTION OF THE PREFERRED EMBODIMENTS

Figure 1:
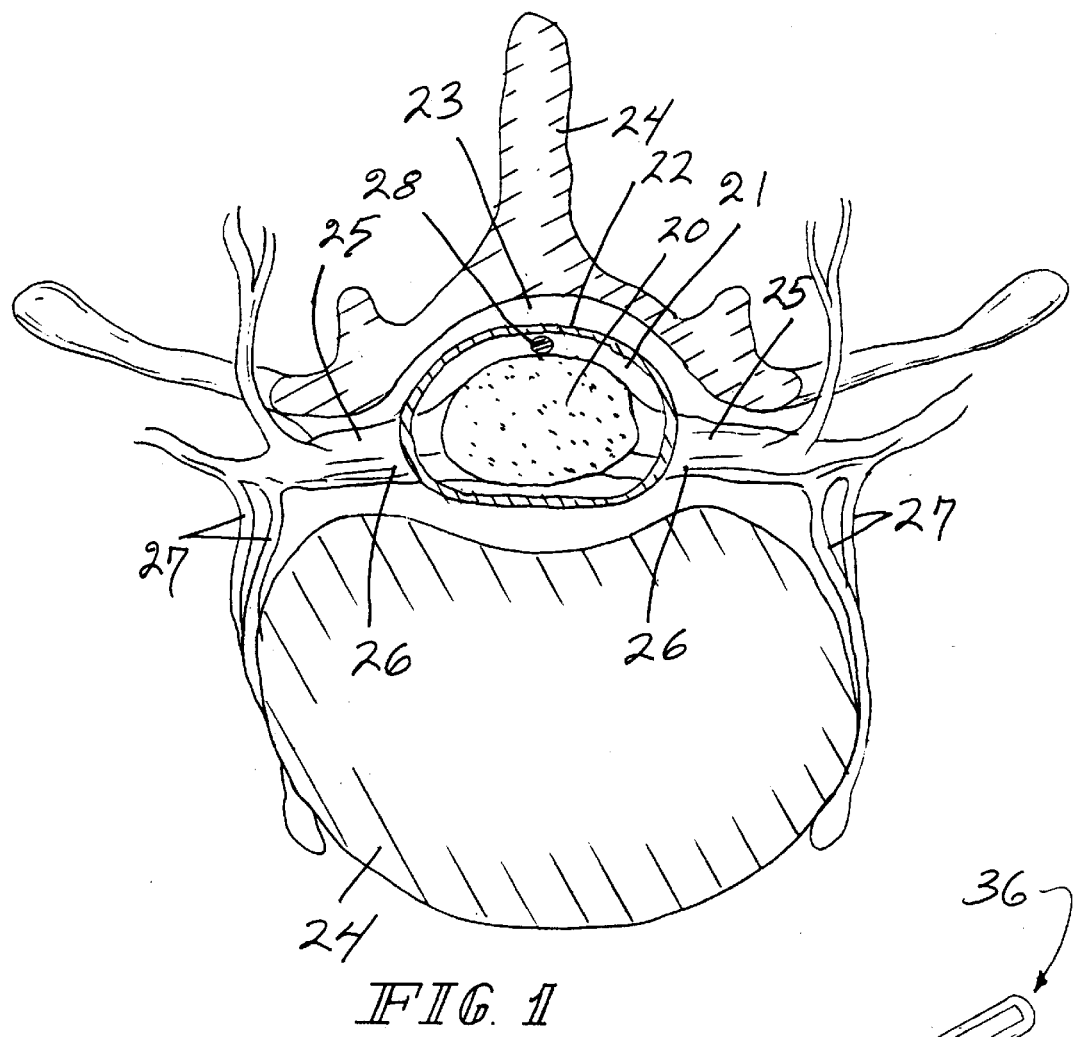
FIG. 1 is a cross-sectional view of a backbone and spinal cord.

Electrodes used for spinal cord stimulation are typically implanted in the epidural space 23 between the vertebra 24 and the dura 22, shown in FIG. 1. This is done for various reasons, including reduced complexity of the surgery, reduced potential complications, an increased stability of the implant. However, implantation in the epidural space requires a significant amount of additional stimulation power since the signal must be transmitted through the dura 22 and epidural space 23 and cerebrospinal fluid in order to reach its desired neural targets in the spinal cord 20. Anterior roots 25 and posterior roots 26 of the spinal cord 20 and Rami Communicantes 27 are also shown.

There were early stimulator leads 28 which were utilized in the intrathecal space 21 between the spinal cord 20 and the dura 22 without success. Typically, these leads resulted in inconsistent stimulation, overstimulation and, generally, ineffective therapy. However, they utilized technology approximately thirty years old. Due to development and implementation of better epidural leads, as well as the lack of a concern for energy requirements (since they were using an external battery pack), this methodology was quickly abandoned.

More recently, intrathecal catheters have been utilized extensively for administration of drugs including morphine and baclofen via implantable drug pumps. Catheter complications were so prevalent thirty years ago (CSF leakage, migration, etc.) are no longer a significant problem. Of course, administration of a drug does not require a precise electrode placement.

This new intrathecal neurostimulation electrode would uses for example four millimeter electrode contacts (more forgiving when it comes to precise electrode placement) and yet would require dramatically less power (less than 20% of the power required for current epidural electrodes) because the electrodes would be in direct contact with the CSF and much closer to the desired neural targets. The primary insulating factor resulting in higher power requirements for epidural leads is the lack of conductivity of the dura 22. The shunting effect of electrical current within the CSF is a much less significant factor. Therefore, an electrode designed with a stabilization means or fixing elements for use in the intrathecal space 21 utilizing materials generally accepted in the art for intrathecal drug administration would provide a unique, novel and advantageous method of stimulation of the spinal cord.

Fixation methods could include one or more of the following: inflatable balloons, tines which are either retractable with a stilet or simply pliable enough to fit through a specially designed introducer or a novel shape (D shape) or the use of nitinol. Any of these fixation methods, singly or in combination, can be used to provide stable electrode placement on a long term basis.

The advantages of an intrathecal electrode are dramatically reduced size and/or increased life of a neurostimulator implant. In addition, implantation in the intrathecal space allows the use of a larger diameter electrode catheter and, therefore, more electrodes can be placed, providing a wider selection of stimulation sites and stimulation paradigms. These stimulation paradigms could include sophisticated programs that switch stimulation between a number of electrodes slowly (over seconds or minutes, hours or days) to avoid accommodation of the stimulation or could be fast (approximately the same speed of the electrical activity of neurons in the spinal cord) artificially generating neural signals along the spinal cord 20 which could be perceived as any other sensory function with signals that travel through the spinal cord. For instance, a signal could be generated that would correspond to heat being applied to a patient's big toe, or pressure being applied to a patient's foot, or the sensation of a limb in a different orientation than it actually is.

Theoretically, tastes, smells, sights or even thoughts could be created in this manner allowing various artificial prosthesis (visual, auditory, etc.) to interface with the human body.

Figure 2:
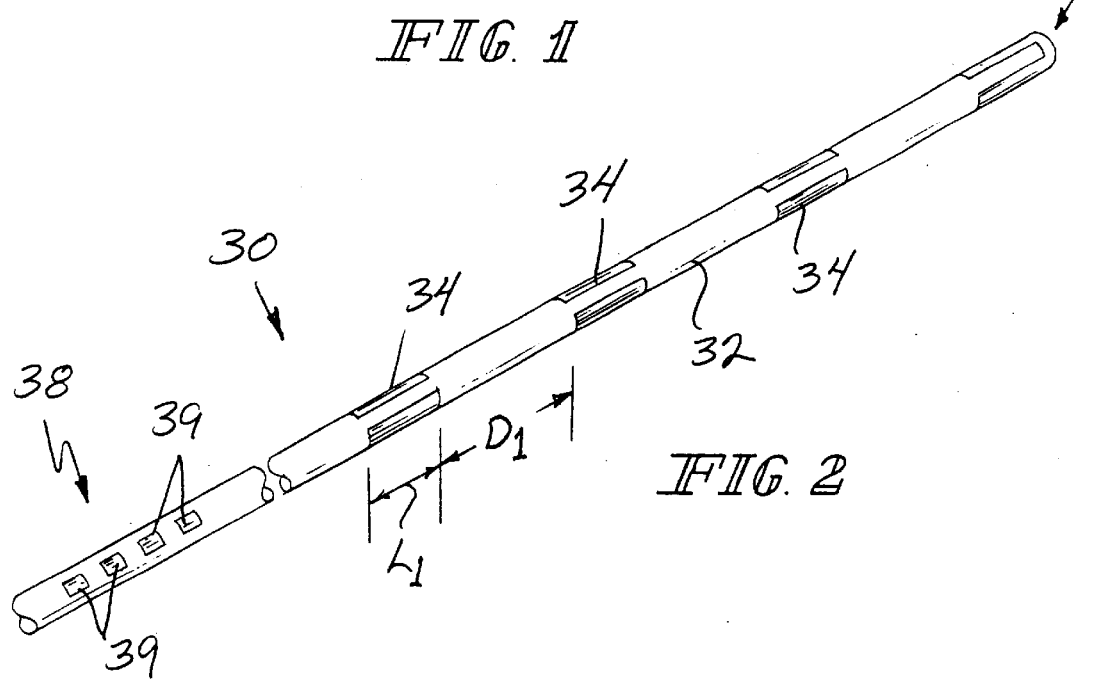
FIG. 2 is a perspective view of a catheter lead having 270° electrodes incorporating the principles of the present invention.

A first embodiment is illustrated in FIG. 2. A catheter lead 30 includes a sheath 32 having a plurality of electrodes 34 at a distal end 36 of the catheter 30. A proximal end 38 of the catheter 30 have contacts 39 to be connected to a stimulator, not shown. There is one contact 39 for each electrode 34. The length of the electrodes $L_1$ are generally two to four millimeters. The distance $D_1$ between the electrodes is typically six millimeters, for example. The electrodes are shown to extend 270 degrees about the circumference of the catheter.

In order to achieve further increases in battery life, the surface area of the active electrode contact can be reduced. An electrode with a specific orientation adjacent to the spinal cord would allow a 30°–270° electrode as opposed to the 360° electrodes used in all current catheter electrodes. This would also enable the electrodes to remain at the preferred three or four millimeters in length making it easier for physicians to hit the desired target and requiring fewer electrode contacts in the lead (also allowing a smaller lead). Different means could be used to stabilize the electrode in place, including (1) inflatable balloons, (2) nitinol, (3) novel shape electrodes, (4) mechanical system whereby tines are deployed upon removal of the stilet, (5) mechanical system of flexible tines.

Figures 3, 3A:
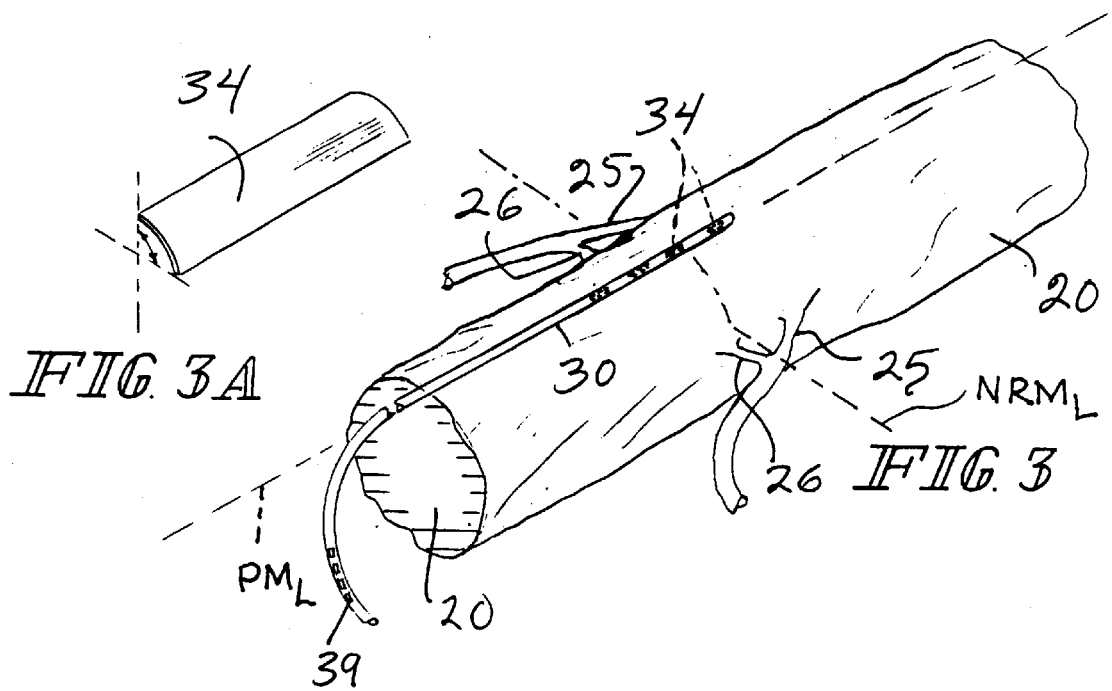
FIG. 3 is a perspective view of a catheter lead with 90° electrodes positioned on the spinal cord.
FIG. 3A is a perspective view of the 90° electrode.
Figures 4, 4A:
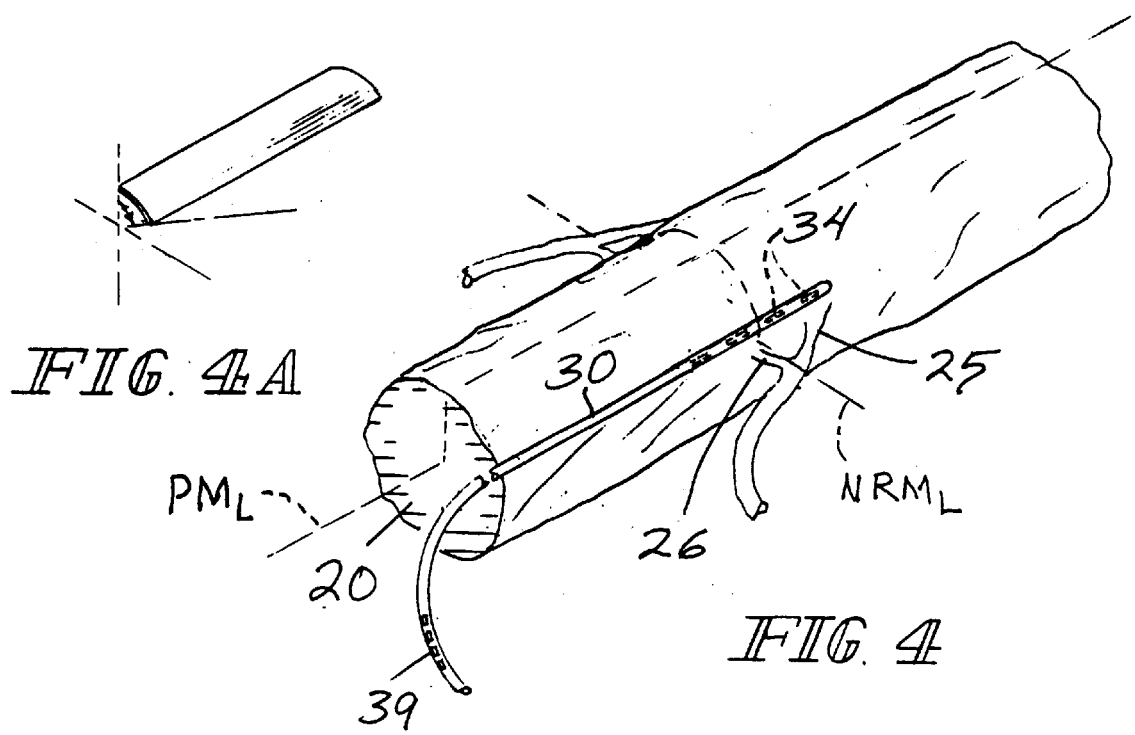
FIG. 4 is a perspective view of a catheter lead with a 60° electrode positioned on the spinal cord.
FIG. 4A is a perspective view of the 60° electrode.

A 270° electrode is illustrated in FIG. 2, a 90° electrode is illustrated in FIG. 3A and a 60° electrode is illustrated in FIG. 4A.

The small radius electrode, for example, 90° or less, allows a focused electrical stimulation field along the physiological midline $PM_L$ of the spinal cord 20 and reduces the effective stimulation field in the area of the bending fibers. As illustrated in FIG. 3, the electrode 34 may also be placed at the nerve root midline $NRM_L$. It is well known that bending fibers are preferentially stimulated when compared to longitudinal fibers. Thus, by positioning the lead adjacent to the desired longitudinal fibers, a focused stimulation of the longitudinal fibers will take place.

The small electrodes in the range of 30°–60° also allows selective activation of the fibers. This is particularly useful where the nerve enters the cord. Such placement is illustrated in FIG. 4, where the 60° electrode 34 is adjacent to the nerve roots 25,26.

For any of the above lead designs, an additional method of decreasing power requirements is to use monopolar stimulation. A large surface area common anode electrode is used in conjunction with a single electrode in the desired stimulation area on the electrode contact array. Monopolar stimulation is not new, but does provide the opportunity to decrease the power requirements for effective stimulation.

The incorporation of a large surface area anode electrode some distance away from the other active electrodes on the same catheter or along the length of an intrathecal catheter has never been performed or attempted. In the prior systems, the casing of the stimulator acted as the anode in a monopolar mode. Its distance from the distal electrodes created a long current path. This new and novel approach reduces the current path, creates a different field and also allows a unitary electrode system so that the stimulator device itself does not have to be made in two different configurations (one with an active case anode and one without). Therefore, a choice between bipolar and monopolar stimulation can be made after implantation using a stimulator (pulse generator) which could normally only provide bipolar stimulation.

As illustrated in FIG. 5, an additional electrode 35 is provided at the distal end 36 displaced from the other electrodes 34. The electrodes 34 are shown as 360° electrodes. As illustrated in FIG. 6, catheter electrode 40 includes a sheath 42 with having a plurality of inline electrodes 44 and an additional electrode 45 on the wire or sheath extension 47 extending from the distal end or paddle 46. The proximal end 48 has contacts 49 connected to each electrode and to a stimulator.

The electrodes 34,44 all have a length L1 and the additional electrode 35,45 has a length L2. Length L2 is greater than L1, at least twice its length. Thus, for example, if length L1 is two millimeters, the length L2 is four millimeters. The length L2 may be anywhere between 2–4 times that of the length L1. Also, it should be noted that the additional electrode 35,45 is spaced by a distance D2 from the nearest electrode 34,44. Where D1 is approximately six millimeters, the distance D2 is at least 10 millimeters and can be as much as 20 millimeters. With this distance, the electrode acts as a point source when used in conjunction with a second electrode. The electrodes 34,44 act as a point source when used in conjunction with the additional electrode 35,45 of the increased area.

Alternatively, a common anode or additional electrode 35 may be the same length as the other electrodes 34, but have a greater circumferential dimension than that of the electrode 34. This would increase the surface area of the additional electrode 35 relative to the other electrodes 34. Therefore, the electrodes 34 may be in the 30° to 270° configuration previously described. The separation difference between the electrodes 34 and that of 35 will allow operation as described with respect to FIGS. 5 and 6. Such an electrode is illustrated in FIG. 12 to be discussed below.

A catheter lead capable of stimulation electrically as well as dispensing drugs is illustrated in FIGS. 7–11. The catheter lead 50 has a sheath 52 with inline electrodes 54 spaced along the distal end 56. At the proximal end 58, terminal contacts 59 are connected internally to each of the electrodes shown. A passage 60 is provided in the sheath 50. In FIG. 7, an outlet 62 is provided in the tip of the distal end 56 and a balloon fixation device 63 is shown. Provision is also made for an optional stilet which is removable and may be used to assist in placement of the catheter. Various stilets 61 of different shapes and characteristics may be used with these leads.

In FIG. 8, the outlet 64 is shown in the space between the electrodes 54 and a nitinol fixation device 65 is shown in the deployed condition. In FIG. 8A, nitinol fixation device 65 is shown prior to the deployment through opening 53 in sheath 52. In FIG. 9, the outlet 64 is shown in or on the electrode 54 and a tine fixation device 67 is shown.

Although one fixation is illustrated on a specific Figure, any fixation device may be used with any of the catheters. Fixation methods may also include devices that are actively deployed and/or retracted (for instance by a stilet) in addition to the methods shown herein. Also, the fixation device may be located at any or more than one location or position along the catheter. A fixation device should be used where the catheter electrode is installed in the intrathecal space.

While FIGS. 7–9 show the passage 60 internal to the sheath 52, an external delivery 68 may be used as shown in FIG. 10.

The electrode catheter 50 may also include a single or pair of optical channels 70 and 72 having outlets or ports in the distal end. The fiberoptic channels and light energy delivered through a clear translucent area in the catheter is illustrated in FIG. 11. One of the channels can provide a source of light to be used as a further source of stimulation. The other channel will form a lens for a camera or other monitoring devices. The camera can be used in positioning the electrode or distal end. Channel 60 with outlet 64 is also shown for a drug delivery.

It should be noted that only a single optical path can be used to provide a source of light for a photon stimulation without the passage 60 or the outlet 64. It should also be noted that the passage 60 or external passage 68 for drug delivery may be used in combination with the light channel 70 without the electrodes 54. Although two channels 70, 72 are shown, any number of channels could be used and could include a combination of different types of channels— working channels for instruments, optical channels for light or camera, stilets etc.

The catheter of FIGS. 7–11 may be used in a percutaneous drug treatment method. The drug is administered to the patient and the stimulation cathode is positioned adjacent the tissue to be treated by the drug. The tissue is then stimulated using the catheter. This allows selective and localized drug treatment. Certain compounds change chemically when stimulated. Compounds can also be delivered via electropheretic means.

The intrathecal location of this catheter places it past the blood/brain barrier and therefore offers numerous unique opportunities for combination stimulation/drug treatment regimes. In addition, application of various forms of energy (heat, cold, etc.) independently or with stimulation allow indirect alteration of brain chemistry. Also the production of heat in a tissue may make the tissue more susceptible to absorption of a drug. The drug may be administered through the passage 60 or 68. The source of stimulation and/or the drugs may be external to the body or totally implantable. The implantable system could include a microprocessor, pump, port and an external port for refilling the pump or selection of a different drug or fluid.

The drug may be stimulated by electrical energy using the electrodes 54 or by photonic energy using the optic channel 70. Heat may be produced by either the electrodes 54 or the optical channel 70. Cold may be produced by a Peltier effect chip or other means, for example gas or liquids. If the drug is responsive to light energy of a specific wavelength, the stimulation uses light energy of that specific wavelength.

Finally, intrathecal stimulation by light energy may be administered via the catheter—with or without drugs or electrical stimulation—to activate certain tissues. These tissues may, in some cases, be treated in some manner to increase their sensitivity to this method of activation and maybe used in combination with electrical stimulation.

The lead 50 as illustrated in FIG. 12 is curved at its distal end 56 which includes the electrodes 54. Sheath 52 includes a wire extension 57 which includes the additional anode electrode 55 and the electrical contact 59. The curved distal end 56 wraps around the spinal cord or the nerves. This is another form of a fixing device. The stilet 61 can be inserted through passage 60 to maintain the distal end 56 linear until it is adjacent to the nerve or the spinal cord. The passage 60 may then be used for fluid delivery.

Figure 14:
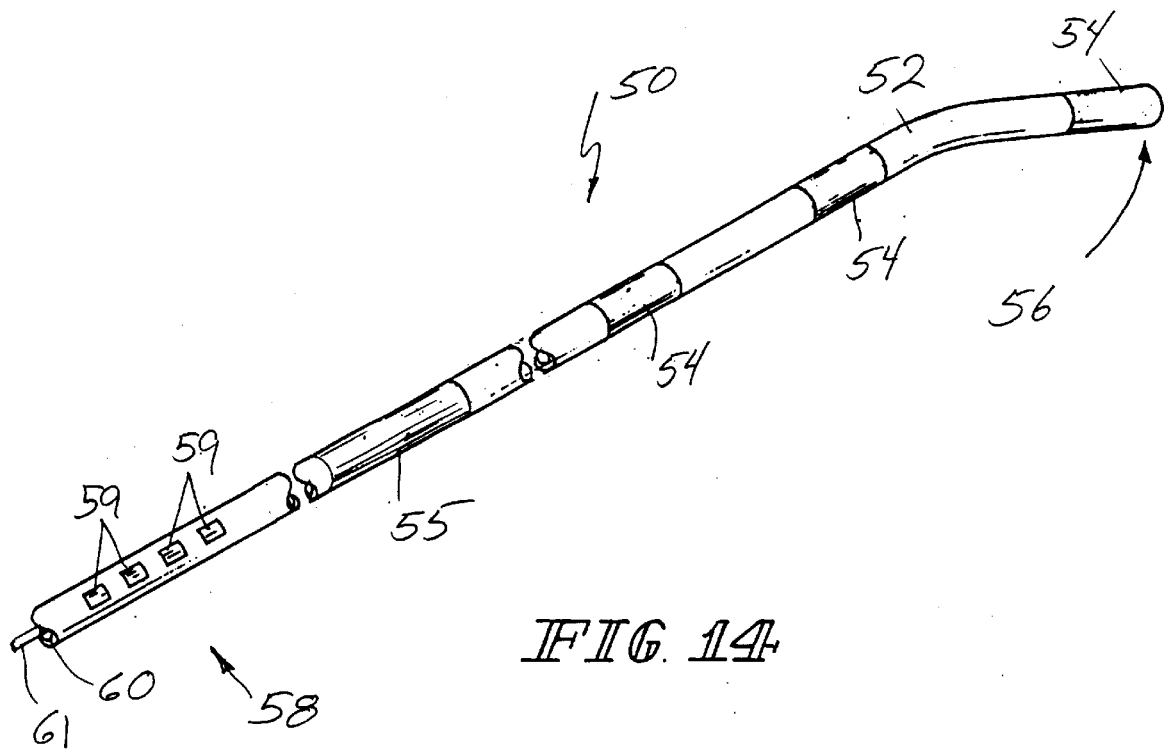
FIG. 14 is a perspective view of a catheter electrode having a bent distal end according to the principles of the present invention.

Different shape stilets may be used (bent tips for example) to improve steerability during positioning of the catheter, as illustrated in FIG. 14.

Additional electrode 55 has the same length L1 along the sheath 52 or wire 57 as does the electrodes 54. The difference is that electrodes 54 are illustrated as 270° electrodes, whereas additional electrode 55 is a 180° electrode. This difference in circumferential dimension provides the difference in surface area. This provides the minimum 2 to 1 surface area as previously discussed. obviously, the distance $D_1$ between electrodes 54 is substantially less than the distance $D_2$ between electrodes 54 and 55.

Figure 13:
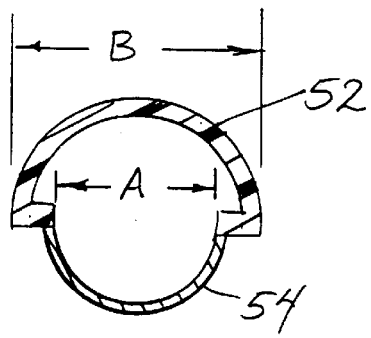
FIG. 13 is a cross-sectional view of another catheter electrode with a 90° electrode of reduced area according to the principles of the present invention.

A modified 90° electrode is illustrated in cross-section in FIG. 13. Electrode 54 has a smaller radius or diameter A than sheath's 52 radius or diameter B. For example, the diameter A may be 0.0045 inches and diameter B may be 0.065 inches. The shape of the sheath and electrode allows introduction through a standard introducer needle. It still offers a reduced area electrode 54 and a stabilizing shape which may be used with or without tines or other fixation means.

Although the invention has been described for use with an implanted stimulator system (externally or internally powered), it should be noted that the same type of regime can be delivered by a non-implantable device. Applications for such non-implantable systems could include intraoperative testing of a stimulator system prior to implantation. An external stimulator system is connected to an implantable electrode for a period of trial stimulation prior to determining whether an implantation should be performed.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. A method of drug treatment comprising:
   positioning a stimulation catheter in the intrathecal space;
   administering drugs via the catheter; and
   stimulating the tissue using the catheter;
   wherein the catheter includes an optical channel with one or more ports at a distal end of the catheter and the stimulation is by photonic energy.

2. The method according to claim 1, wherein the catheter includes a passage with one or more ports at a distal end of the catheter and the drug is administered through the passage.

3. A method of drug treatment comprising:
   positioning a stimulation catheter in the intrathecal space;
   administering drugs via the catheter; and
   stimulating the tissue using the catheter;
   wherein the drug administered is selected to be responsive to stimulation.

4. The method according to claim 3, wherein the catheter includes one or more electrodes at the distal end and the stimulation is by electric energy.

5. The method according to claim 3, wherein the drug administered is responsive to light energy of a specific wave length and including stimulating the tissue with light energy of the specific wave length using the catheter.

6. The method according to claim 3, wherein the drug administered is responsive to heat and including stimulating the tissue with heat using the catheter.

7. The method according to claim 3, wherein the drug administered is responsive to cold and including stimulating the tissue with cold using the catheter.

8. The method according to claim 3, wherein the catheter includes an optical channel with a port at a distal end of the catheter and the catheter is positioned using the optical channel.

* * * * *